United States Patent [19]

O'Lenick, Jr.

[11] Patent Number: 4,868,236

[45] Date of Patent: Sep. 19, 1989

[54] CITRATE POLYESTERS OF GUERBET OF ALCOHOLS AND THEIR ALKOXYLATES AS POLYCARBONATE LUBRICANTS

[76] Inventor: Anthony J. O'Lenick, Jr., 743 Ridgeview Dr., Lilburn, Ga. 30247

[21] Appl. No.: 300,473

[22] Filed: Jan. 23, 1989

[51] Int. Cl.$^4$ .................. C07C 69/704; C08K 5/11
[52] U.S. Cl. ........................... 524/308; 524/311; 524/611; 560/180; 560/182; 560/185; 560/190; 560/198; 560/199
[58] Field of Search ............. 560/180, 182, 198, 199, 560/190, 185; 524/311, 611, 308

[56] References Cited

U.S. PATENT DOCUMENTS

| | | | |
|---|---|---|---|
| 2,046,150 | 6/1936 | Cox et al. | 560/182 |
| 2,815,368 | 12/1957 | Matuszak | 560/185 |
| 2,991,273 | 7/1961 | Hechelhammer | 528/201 |
| 2,999,835 | 9/1961 | Goldberg | 524/267 |
| 3,025,271 | 3/1962 | Borchert | 560/180 |
| 3,028,365 | 4/1962 | Schnell et al. | 528/202 |
| 3,102,128 | 8/1963 | Hennig et al. | 560/180 |
| 3,148,172 | 9/1964 | Fox | 528/202 |
| 3,239,555 | 3/1966 | Miksch et al. | 560/180 |
| 3,271,367 | 9/1966 | Schnell et al. | 528/171 |
| 3,271,368 | 9/1966 | Goldberg et al. | 528/174 |
| 3,280,078 | 10/1966 | Hostettler et al. | 528/271 |
| 3,396,121 | 8/1968 | Miksch et al. | 560/180 |
| 3,544,514 | 12/1970 | Schnell et al. | 528/274 |
| 3,567,784 | 3/1971 | Tsatos et al. | 568/625 |
| 3,784,595 | 1/1975 | Schirmer et al. | 528/202 |
| 4,007,150 | 2/1977 | Adelmann et al. | 524/611 |
| 4,065,436 | 12/1977 | Adelmann et al. | 528/486 |
| 4,081,495 | 3/1978 | Freitag et al. | 525/470 |
| 4,097,435 | 6/1978 | Rawlings et al. | 524/277 |
| 4,131,575 | 12/1978 | Adelmann et al. | 528/196 |
| 4,143,024 | 3/1979 | Adelmann et al. | 524/291 |
| 4,171,455 | 10/1979 | Tomita et al. | 568/625 |
| 4,299,994 | 11/1981 | Stabel | 568/625 |
| 4,425,458 | 1/1984 | Lindmer et al. | 524/314 |
| 4,731,190 | 3/1988 | O'Lenick et al. | 252/49.3 |
| 4,767,815 | 8/1988 | O'Lenick | 524/318 |

Primary Examiner—Veronica P. Hoke

[57] ABSTRACT

The invention deals with the preparation, compositions, and application of certain high molecular weight hydrophobic citrate polyesters of guerbet alcohols and their alkoxylates, which are useful in polycarbonate processing.

10 Claims, No Drawings

CITRATE POLYESTERS OF GUERBET OF ALCOHOLS AND THEIR ALKOXYLATES AS POLYCARBONATE LUBRICANTS

BACKGROUND OF THE INVENTION

1. Field of the Invention

The present invention deals with the preparation, compositions, and application of certain high molecular weight hydrophobic guerbet citrate polyesters which are useful in polycaronate processing.

2. Description of the Art Practices

It is known that esters of simple alcohols may be used for various purposes including polycarbonate processing. In U.S. Pat. No. 3,784,595 issued Jan. 8, 1974 to Schirmer et al polycarbonate molding compositions are shown which are based on the esters of a trihydric alcohol and a saturated aliphatic carboxylic acid, U.S. Pat. No. 4,065,436 issued to Adelmann in December 1977 describes thermoplastic molding compositions containing a mold release agent which is an ester of a saturated aliphatic carboxylic acid having from 10 to 20 carbon atoms per molecule and an aromatic hydroxy compound containing from 1 to 6 hydroxyl groups.

It is also known from U.S. Pat. No. 4,097,435 issued June 27, 1978 to Rawling et al that montanic acid ester waxes may be employed in polycarbonate molding compositions. U.S. Pat. No. 4,131,575 issued Dec. 26, 1978 to Adelmann describes in combination with aromatic polycarbonates, mold release agents which are the esters of saturated aliphatic carboxylic acids with alcohol containing from 4 to 6 hydroxyl groups. The disclosures of U.S. Pat. No. 4,131,575 are also found in the related British Patent No. 1,490,467 published Nov. 2, 1977. U.S. Pat. No. 4,143,024 issued Mar. 6, 1979 to Adelmann et al describes aromatic polycarbonate based thermoplastic molding compositions utilizing as a mold release agent the ester of a saturated aliphatic carboxylic acid containing from 10 to 20 carbon atoms per molecule and an aromatic hydroxyl compound from having 1 to 6 hydroxyl groups.

Lindner et al, U.S. Pat. No. 4,425,458, issued Jan. 10, 1984, teaches that specific guerbet alcohol diesters containing from 16 to 40 carbon atoms total in the guerbet alcohol molecule can be used as mold release agents in polycarbonate products.

U.S. Pat. #4,767,815 issued Aug. 30, 1988 to O'-Lenick teaches that two mole equivalents of a guerbet alcohol can be reacted with butryolactone to form a ether ester which can be used as a polycarbonate lubricant.

General disclosures of polycarbonate technology are found in U.S. Pat. No. 4,081,495 issued Mar. 28, 1978 to Freitag et al. Similar general disclosures are also found in U.S. Pat. No. 4,007,150 issued to Adelmann et al on Feb. 8, 1977.

To the extent that each of the foregoing patents is relevant to the present invention they are herein specifically incorporated by reference. Throughout the specification and claims, percentages and ratios are by weight, pressures are gauge and temperatures are Celsius unless otherwise noted.

SUMMARY OF THE INVENTION

The present invention is directed to a series of high molecular weight highly branched citrate esters, useful as a mold release agent for polycarbonate resin compositions. The esters are the reaction product of a guerbet alcohol or a guerbet alcohol alkoxylate, citric acid and in a subsequent step a crosslinking diacid.

Another aspect of the invention is a novel guerbet triester of citric acid, which is the precursor molecule for the compounds of this invention.

Another apsect of the invention is a proces used to prepare of the esters. Still another aspect of the invention is the process for the use of these novel products in polycarbonate and other thermoplastic molding processes.

DETAILED DESCRIPTION OF THE INVENTION

The present invention described molecules that are guerbet citrate polyoxyalkylene esters. The guerbet alcohol portion of the present invention is particularly important in that polycarbonate resins have a high requirement for clarity as they are often used to form clear articles including safety glasses. Unfortunately, the polycarbonate resins tend to fail to release when molded, therefore agents must be employed to assist in releasing the polycarbonate resin from the mold. A substantial difficulty which has been found in the art is to ensure that the polycarbonate resin is not adversely affected by the mold release agent. Incorporation of polyoxypropylene and or polyoxyethylene into the ester results in increased polymer stability by minimizing free radical degradation and thereby increasing optical stability properties of the polycarbonate.

The molecules of this invention conform to the following generic structure:

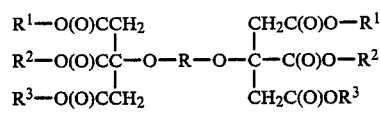

wherein:

R is selected from;

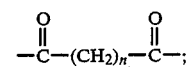

or

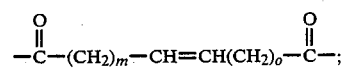

n has a value from 1 to 15;
m and o independently range from 0 to 5;
$R^1$, $R^2$ and $R^3$ are independently selected from

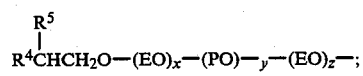

wherein $R^4$ and $R^5$ may be the same or different saturated aliphatic groups; EO is ethylene oxide: PO is a propylene oxide group; x, y and z are independently between 1 and 10. Ethylene oxide and propylene oxide may be added in blocks or random manner by premixing the oxides.

In a preferred range $R^4$ and $R^5$ each independently range from $C_6H_{13}$ to $C_{10}H_{21}$ and x, y and z each independently range from 0 to 10.

It will be observed in the present invention that the mold release agents of this invention result in polycarbonate products in which the clarity is not adversely affected. The guerbet citrate esters of the present invention are observed to migrate sufficiently from the polycarbonate resin to the surface of the mold to effect release. These guerbet citrate polyoxyalkylene esters do not substantially sweat out or collect on the surface of the molded articles. Sweating out cause hazing which is a disadvantage for mold mold release agents. Another important aspect in working with mold release agents is the volatility of the compounds. It will of course be observed that the molding process requires large amounts of heat to liquefy the polycarbonate. This turn requires low volatility of the mole release agent so that the mold release agent is not lost to the atmosphere before it can function. It is also noted that an air pollution problem within a plant may arise where a mold release agent of high volatility is utilized. The products of the present invention will be observed to have low volatility thus presenting a distinct advantage over low molecular weight materials.

Guerbet alcohols have been known since the 1890's when Marcel Guerbet first synthesized these materials (M. Guerbet, C.R. Acad. Sci. Paris, 128, 511; 1002 (1899)). These materials are high in molecular weight and are liquid even at very low temperatures.

The guerbet alcohols used in a preferred embodiment of the present invention contain from about 12 to 40 carbon atoms (total) in the guerbet alcohol molecule.

It is known in the art that guerbet alcohols may be formed from the same or different alcohols i.e. a homo or hetero system. That is, a guerbet alcohol is the condensation product of two molecules joined at the beta carbon of the alcohol which has retained the hydroxyl functionality. The resultant product is therefore a highly branched primary alcohol containing a single hydroxyl group. It is possible to obtain mixtures of alcohols and to condense them into hetero systems. It is also possible to obtain products which are guerbet alcohols from a short chained alcohol. It is desired for reasons of polarity, compatibilty with and solubility in the polycarbonate system that homo-guerbet alcohols having between 16 and 40 carbon atoms be used.

The polycarbonates with which the present guerbet citrate esters are effective mold release agents include homopolycarbonates and copolycarbonates which are based, for example, or one or more of the following bisphenols: hydroquinone, resorcinol, dihydroxydiphenyls, bis-(hydroxyphenyl)-alkanes. bis-(hydroxyphenyl)-cycloalkanes, bis-(hydroxylphenyl)-sulphides, bis-(hydroxyphenyl)-ethers, bis-(hydroxylphenyl)-ketones bis-(hydroxyphenyl)-sulphoxides, bis-(hydroxyphenyl)-sulphones and alpha, alpha-bis(hydroxyphenyl)-diisopropyl-benzenes, as well as their nuclear alkylated and nuclear-halogenated compounds. These are further suitable aromatic dihydroxy compounds are described, for example, in U.S. Pat. Nos. 3,028,365, 2,999,835, 3,148,172, 3,271,368, 2,991,273, 3,271,367, 3,280,078, 3,014,891 and 2,999,846, in German Offenlegungsschriften (German Published Specifications) Nos. 1,570,703, 2,063,050, 2,063,052, 2,211,956, and 2,211,957, in French Patent Specification No. 1,561,518 and in the monograph "H. Schnell, Chemistry and Physics of Polycarbonates, Interscience Publishers, New York, 1964".

Preferred bisphenols are those of the formula I shown below:

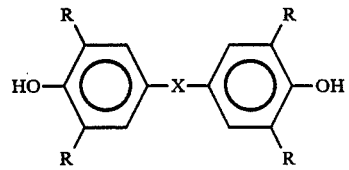

in which R is identical or different and denotes H. $C_1$-alkyl, Cl or Br, and in which X is a bond, $C_1C_8$-alkylene, $C_2$-alkylidene, $C_5$–$C_{15}$cycloalkylene, $C_5$–$C_{15}$-cycloalkylidene, —SO— or formula II shown below:

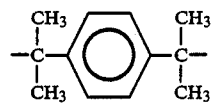

Examples of these bisphenols are 4,4'-dihydroxydiphenyl, 2,2-bis-(4-hydroxyphenyl)-propane, 2,4-bis(4-hydroxyphenyl)-2-methylbutane, 1,1-bis-(4-hydroxyphenyl)-cyclohexane, a,a-bis(4-hydroxyphenyl)-p-diisopropylbenzene. 2,2-bis-(3-methyl-4-hydroxyphenyl)-propane, 2,2-bis-(3-chloro-4-hydroxyphenyl)-propane, bis-(3,5-dimethyl-4-hydroxyphenyl)-propane, bis(3,5)-dimethyl-4-hydroxyphenyl)-2-methylpropane, 1,1-bis-(3,5-dimethyl-4-hydroxyphenyl)-cyclohexane, a,a-bis-(3,5-dimethyl-4-hydroxyphenyl)-p-diisopropyl-benzene, 2,2-bis-(3,5-dichloro-4-hydroxyphenyl)-propane and 2,2-bis(3,5-dibromo-4-hydroxyphyenyl)-propane.

Examples of particularly preferred bisphenols are: 2,2-bis-(4-hydroxyphenyl)-propane, 2,2-bis(3,5-dimethyl-4-hydroxyphenyl)-propane, 2,2-bis-(3,5-dichloro-4-hydroxyphenyl)-propane, 2,2-bis-(3,5-bibromo-4-hydroxyphenyl)-propane, and 1,1-bis-(4-hydroxyphenyl)-cyclohexane.

Preferred aromatic polycarbonates are those which are based on one or more of the bisphenols mentioned as being preferred. Particularly preferred copolycaronates are those based on 2,2-bis-(4hydroxyphenyl)-propane and one of the other bisphenols mentioned as being particularly preferred. Further particularly preferred polycarbonates are those based solely on 2,2-bis-(4-hydroxyphenyl)-propane or 2,2-bis-(3,5-dimethyl-4-hydroxyphenyl)-propane.

The aromatic polycarbonates can be prepared in accordance with known processes, such as, for example, in accordance with the melt trans-esterification process from bisphenols and diphenyl carbonate and the two-phase boundary process from the bisphenols and phosgene, as described in the above-mentioned literature.

The aromatic high-molecular weight polycarbonates can be branched due to the incorporation of small amounts, preferably of between 0.05 and 2.0 mol % (relative to diphenols employed), of trifunctional or more than trifunctional compounds, especially compounds with three of more phenolic hydroxyl groups.

Polycarbonates of this type are described, for example, in German Offenlegungsschriften (German Published Specifications) Nos. 1,570,533, 1,595,762, 2,116,974 and 2,113,347; British Patent Specification No. 1,079,821; U.S. Pat. No. 3,544,514 and German Patent Application No. P25 00 092.4.

Somes examples of compounds with three or more than three phenolic hydroxyl groups which can be used are phloroglucinol, 4,6-dimethyl-2,4,6-tri-(4,hydroxyphenyl)-heptane, 2,4,6-trimethyl-2,4,6-tri-(4-hydroxyphenyl)-heptane, 1,4,5-tri-(4-hydroxyphenyl)-benzene, 1,1,1-tri-(4-hydroxyphenyl)-ethane, tri-(4-hydroxyphenyl)-phenylmethane, 2,2-bis-(4,4-bis-(4-hydroxyphenyl)-cyclohexyl)-propane, 2,4-bis-(4-hydroxyphenylisopropyl)-Phenol, 2,6-bis-(2-hydrox-5-methylbenzyl)-4-methyphenol, 2-(4-hydroxyphenol), 2-2,4dihydroxyphenyl)-propane, hexa(4-4-hydroxyphenylisopropyl)phenyl)orthoterephthalic acid ester, tetra-(4-hydroxyphenyl)-methane and 1,4-bis-((4',4''-dihydroxytriphenyl)methyl)-benzene. Some of the other trifunctional compounds are 2,4-dihyroxybenzoic acid, trimesic acid, cyanuric chloride and 3,3-bis-(4-hydroxyphyenyl)-2oxo-2,3-dihydroindole.

The aromatic high-molecular polycarbonates should as a rule have mean weight-average molecular weights M of at least 10,000; especially of 10,000 to 200,000; preferably of 20,000 to 80000; determined by measuring the relative viscosity in $CH_2Cl_2$ at 25 degrees c. and a concentration of 0.5% by weight.

The thermoplastic polycarbonate molding compositions find use in several areas. Such examples of use for the polycarbonates of the present invention utilizing the mold release agents include the electrical industry and the optical field such as the stripping of sockets, coiled bodies, complicated housings, projector housings, switch cabinet bottoms and other similar applications.

The mold release agent of the present invention (the guerbet polyoxyalkylene citrate ester) is utilized with the polycarbonate in the manner of similar prior polycarbonate formulations. The level of use of the guerbet citrate ester to the polycarbonate is from about 0.25% to about 1.0%; preferably from about 0.1% to about 0.25% by weight of the total polycarbonate compositions.

Raw Materials

Guerbet Alcohols and Alkoxylates

The Guerbet alcohols used as raw materials are items of commerce and are prepared by processes known to those skilled in the art. They are produced by several manufacturers including; Exxon Chemicals Corporation (Darien, Conn.) and Henkel Corporation (Ambler, Pa.).

The alcohols were ethoxylated using standard procedures known to those skilled in the art. Reference is drawn to U.S. Pat. No. 4,731,190 to O'Lenick, Jr. et al. The reference teaches the alkoxylation processes for guerbet alcohols.

$$R^4CHCH_2O-(EO)_x-(PO)_y-(EO)_z-$$
$$\underset{R_5}{|}$$

| Example | $R^4$ | $R^5$ | x | y | z |
|---|---|---|---|---|---|
| 1 | C8 | C10 | 0 | 0 | 0 |
| 2 | C8 | C10 | 1 | 1 | 1 |
| 3 | C8 | C10 | 0 | 5 | 2 |
| 4 | C8 | C10 | 5 | 5 | 5 |
| 5 | C8 | C10 | 10 | 10 | 10 |
| 6 | C11 | C13 | 0 | 0 | 0 |
| 7 | C11 | C13 | 1 | 1 | 1 |
| 8 | C11 | C13 | 0 | 5 | 2 |
| 9 | C11 | C13 | 5 | 5 | 5 |
| 10 | C11 | C13 | 10 | 10 | 10 |
| 11 | C16 | C18 | 0 | 0 | 0 |
| 12 | C16 | C18 | 1 | 1 | 1 |
| 13 | C16 | C18 | 0 | 5 | 2 |
| 14 | C16 | C18 | 5 | 5 | 5 |
| 15 | C16 | C18 | 10 | 10 | 10 |

Citric Acid $$\begin{array}{c} CH_2COOH \\ | \\ HO-C-COOH \\ | \\ CH_2COOH \end{array}$$

Fatty Diacids (for crosslinking)

| | |
|---|---|
| Adipic Acid | $HO(O)C(CH_2)_4C(O)OH$ |
| Succinic Acid | $HO(O)C(CH_2)_2C(O)OH$ |
| Dodecanedioic Acid | $HO(O)C(CH_2)_{10}C(O)OH$ |
| Malic Acid | $HO(O)CCH=CHC(O)OH$ |
| Malonic Acid | $HO(O)C(CH_2)_3C(O)OH$ |
| Azelaic Acid | $HO(O)C(CH_2)_5C(O)OH$ |

The compounds of this invention are prepared by reacting citric acid (anhydrous) with a guerbet alcohol or guerbet alcohol alkoxylate to give an intermediate product which is reacted with a polyacid to provide a crosslinked ester. Suitable diacids include: adipic, succinic, maleic, azelic, dodecanedioic, and fumaric.

Reaction Conditions

The esterification can be run without catalyst; however, when no catalysts used reaction rates are inefficient. Standard esterification catalysts are generally used at concentrations of between 0.05% to 0.50% with a preferred range of 0.1% to 0.3%. Catalysts which are effective include but are not limited to: sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. Preferred is stannous oxylate. The reaction is conducted at between 140 and 240 C. under an inert nitrogen blanket. Preferred temperature range is between 180 and 210 C. Water is removed from the reaction which is done using a nitrogen sparge or vacuum of up to 10 mm.

The following are suggested embodiments of present invention.

EXAMPLE 16

To a suitable reaction vessel is added 900.0 grams of guerbet alcohol example 1, 192.0 grams of citric acid and 2.0 grams of stannous oxylate catalyst. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

EXAMPLE 17

To a suitable reaction vessel is added 1341.0 grams of guerbet alkoxylate example #2, 192.0 grams of citric acid, and 2.0 grams of tin oxide catalyst. The temperature is then increased to 160-200 C. while a nitrogen sparge is applied. Water begins to distill off at about 160 C. Vacuum is applied to keep the by-product water distilling. When 97% of the theoretical water is removed the reaction is cooled. The desired product is obtained without and additional purification.

EXAMPLE 18

To a suitable reaction vessel is added 192.0 grams of citric acid, 2049.0 grams of the guerbet alkoxylate example #3 and 2.0 grams of p toluene sulfonic acid catalyst. The temperature is then increased to 160-200 C. A nitrogen sparge is applied during heating. Water begins to distill off at about 160 C. Vacuum is applied to keep the by-product water distilling. When 97% of the theoretical water is removed the reaction is cooled. The desired product is obtained without and additional purification.

EXAMPLE 19

To a suitable reaction vessel is added 192.0 grams of citric acid, 3105.0 grams of guerbet alkoxylate example #4 and 4.0 grams of stannous oxylate catalyst. A nitrogen sparge is then applied. The temperature is then increased to 160-200 C. and by-product water begins to distill off. Vacuum is applied to keep the water distilling. When 97% of the theoretical water is removed the reaction is cooled. The desired product is obtained without and additional purification.

EXAMPLE 20

To a suitable reaction vessel is added 5310.0 grams of guerbet alkoxylate example #5; 192.0 grams of citric acid and 5.0 grams of Tyzor catalyst. The temperature is then increased by 160-200 C., under nitrogen sparge. By-product water begins to distill off. Vacuum is applied to keep the water distilling. When 97% of the theoretical water is removed the reaction is cooled. The desired product is obtained without and additional purification.

EXAMPLE 21

To a suitable reaction vessel is added 192.0 grams of citric acid, 2.0 grams of stannous oxylate catalyst and 1149.0 grams of guerbet alcohol example #6. A nitrogen sparge is applied. The temperature is then increased to 160-200 C. and water begins to distill off. Vacuum is applied to keep the water distilling. When 97% of the theoretical by-product water is removed the reaction is cooled. The desired product is obtined without and additional purification.

EXAMPLE 22

To a suitable reaction vessel is added 192.0 grams of citric acid, 2.0 grams of p. toluene sulfonic acid catalyst and 1590.0 grams of the guerbet alkoxylate example #7. The temperature is then increased to 160-200 C. and by-product water begins to distill off. Vacuum is applied to keep the water distilling off. When 97% of the theoretical water is removed the reaction is cooled. The desired product is obtained without and additional purification.

EXAMPLE 23

To a suitable reaction vessel is added 192.0 grams of citric acid, 2298.0 grams of guerbet alkoxylate example #8 and 2.0 grams of esterification catalyst. The temperature is then increased to 160-200 C. under nitrogen sparge. Water begins to distill off at about 160 C. Vacuum is applied to keep the by-product water distilling. When 97% of the theoretical water is removed the reaction is cooled. The desired product is obtained without and additional purification.

EXAMPLE 24

To a suitable reaction vessel is added 192.0 grams of citric acid. 3354 grams of guerbet alkoxylate example #9 and 2.0 grams of p toluene sulfonic acid catalyst. The temperature is then increased to 160-200 C. and by-product water begins to distill. Vacuum is applied to keep the water distilling. When 97% of the theoretical water is removed the reaction is cooled. The desired product is obtained without and additional purification.

EXAMPLE 25

To a suitble reaction vessel is added 5550.0 grams of guerbet alkoxylate example #10, 192.0 grams of citric acid and 5.0 grams of stannous oxylate catalyst. A Nitrogen sparge is applied. The temperature is then increased to 160-200 C. and by-product water begins to distill off. Vacuum is applied to keep the water distilling. When 97% of the theoretical water is removed the reaction is cooled. The desired product is obtained without and additional purification.

EXAMPLE 26

To a suitable reaction vessel is added 192.0 grams of citric acid, 1569.0 grams of guerbet alcohol example #11, 2.0 grams of an esterification catalyst. The temperature is then increased to 160-200 C. and by-product water begins to distill. Vacuum is applied to keep the water distilling off. When 97% of the theoretical water is removed the reaction is cooled. The desired product is obtained without and additional purification.

EXAMPLE 27

To a suitable reaction vessel is added 2010.0 grams of guerbet alkoxylate example #12; 192.0 grams of citric acid and 2.0 grams of stannous oxylate catalyst. A nitrogen sparge is applied. The temperature is then increased to 160-200 C. and by-product water begins to distill. Vacuum is applied to keep the water distilling off. When 97% of the theoretical water is removed the reaction is cooled. The desired product is obtained without and additional purification.

EXAMPLE 28

To a suitable reaction vessel is added 192.0 grams of citric acid, 2.0 grams of stannous oxylate catalyst, and 2718.0 grams of guerbet alkoxylate example #13. The temperature is then increased to 160-200 C., under a nitrogen sparge. Water begins to distill. Vacuum is applied to keep the by-product water distilling off. When 97% of the theoretical water is removed the reaction is cooled. The desired product is obtained without and additional purification.

EXAMPLE 29

To a suitable reaction vessel is added 192.0 grams of citric acid. 2.0 grams of p toluene sulfonic acid catalyst and 3774.0 grams of guerbet alkoxylate example #14. The temperature then is increased to 160-200 C. and by-product water begins to distill off. Vacuum is applied to keep the water distilling off. When 97% of the theoretical water is removed the reaction is cooled. The desired product is obtained without and additional purification.

EXAMPLE 30

To a suitable reaction vessel is added 5979.0 grams of guerbet alkoxylate example #15, 2.0 grams of stannous oxylate catalyst and 192.0 grams of citric acid. The temperature is then increased to 160-200 C., under nitrogen sparge. Water begins to distill. Vacuum is applied to keep the by-product water distilling off. When 97% of the theoretical water is removed the reaction is cooled. The desired product is obtained without and additional purification.

EXAMPLE 31

To a suitable reaction vessel is added 192.0 grams of citric acid, 2.0 grms of p toluene sulfonic acid catalyst, 450.0 grams of guerbet alcohol example #1; and 2,989.5 grams of guerbet alkoxylate example #15. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 32

To a suitable reaction vessel is added 192.0 grams of citric acid, 2.0 grams of stannous oxylate catalyst, 775 grams of guerbet alkoxylate example #10, and 784.5 grams of guerbet alcohol example #11. A nitrogen sparge is then applied. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 33

To a suitable reaction vessel is added 192.0 grams of citric acid, 300 grams of guerbet alcohol example #1, 379.0 grams of guerbet alcohol example #6, 517.8 grams of guerbet alcohol example #11 and 12.0 grams of stannous oxylate catalyst. A nitrogen sparge is then applied. The temperature is increased to 160–200 C. and by-product water begins to distill off. Vacuum is applied to keep the water distilling off. When 97% of the theoretical water is removed the reaction is cooled. The desired product is obtained without and additional purification.

EXAMPLE 34

To a suitable reaction vessel is added 192.0 grams of citric acid, 2.0 grams of tin oxide catalyst, 1768.0 grams of guerbet alkoxylate example #5, 1831.0 grams of guerbet alkoxylate example #10, and 1973 grams of guerbet alkoxylate example #15. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 35

To a suitable reaction vessel is added 146.0 grams of adipic acid, 2.0 grams of tin oxide catalyst, 436.0 grams of guerbet alkoxylate ester example #16. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 36

To a suitable reaction vessel is added 146.0 grams of adipic acid, 2.0 grams of tin oxide catalyst, 583.0 grams of guerbet alkoxylate ester example #17. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 37

To a suitable vessel is added 146.0 grams of adipic acid, 2.0 grams of tin oxide catalyst. 775.0 grams of guerbet alkoxylate ester example #18. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 38

To a suitable reaction vessel is added 146.0 grams of adipic acid, 2.0 grams of tin oxide catalyst, 1171.0 grams of guerbet alkoxylate ester example #19. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 39

To a suitable reaction vessel is added 146.0 grams of adipic acid, 2.0 grams of tin oxide catalyst, 1906.0 grams of guerbet alkoxylate ester example #20. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 40

To a suitable reaction vessel is added 146.0 grams of adipic acid, 2.0 grams of tin oxide catalyst, 520.0 grams of guerbet alkoxylate ester example #21. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 41

To a suitable reaction vessel is added 146.0 grams of adipic acid, 2.0 grams of tin oxide catalyst, 667.0 grams of guerbet alkoxylate ester example #22. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 42

To a suitable reaction vessel is added 146.0 grams of adipic acid, 2.0 grams of tin oxide catalyst, 859.0 grams of guerbet alkoxylate ester example #23. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 43

To a suitable reaction vessel is added 146.0 grams of adipic acid, 2.0 grams of tin oxide catalyst, 1255.0 grams of guerbet alkoxylate ester example #24. The temperature is then increased to 160–200 C. and by-product

EXAMPLE 44

To a suitable reaction vessel is added 146.0 grams of adipic acid, 2.0 grams of tin oxide catalyst, 1990.0 grams of guerbet alkoxylate ester example #25. The temperature is then increased to 160–200 C. and by-products water begins to distill off. Vacuum is applied to keep the water distilling off. When 97% of the theoretical water is removed the reaction is cooled. The desired product is obtained without and additional purification.

EXAMPLE 45

To a suitable reaction vessel is added 146.0 grams of adipic acid, 2.0 grams of tin oxide catalyst, 660.0 grams of guerbet alkoxylate ester example #26. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 46

To a suitable reaction vessel is added 146.0 grams of adipic acid, 2.0 grams of tin oxide catalyst, 837.0 grams of guerbet alkoxylate ester example #27. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 47

To a suitable reaction vessel is added 146.0 grams of adipic acid, 2.0 grams of tin oxide catalyst, 999.0 grams of guerbet alkoxylate ester example #28. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 48

To a suitable reaction vessel is added 146.0 grams of adipic acid, 2.0 grams of tin oxide catalyst, 1395.0 grams of guerbet alkoxylate ester example #29. The temperature is then increased to 160–200 C. and by-production water begins to distill off. Vacuum is applied to keep the water distilling off. When 97% of the theoretical water is removed the reaction is cooled. The desired product is obtained without and additional purification.

EXAMPLE 49

To a suitable reaction vessel is added 146.0 grams of adipic acid, 2.0 grams of tin oxide catalyst, 2130.0 grams of guerbet alkoxylate ester example #30. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 50

To a suitable reaction vessel is added 230.0 grams of dodecanedioic acid, 2.0 grams of tin oxide catalyst, 436.0 grams of guerbet alkoxylate ester example #16. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 51

To a suitable reaction vessel is added 230.0 grams of dodecanedioic acid, 2.0 grams of tin oxide catalyst, 583.0 grams of guerbet alkoxylate ester example #17. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 52

To a suitable reaction vessel is added 230.0 grams of dodecanedioic acid, 2.0 grams of tin oxide catalyst, 775.0 grams of guerbet alkoxylate ester example #18. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 53

To a suitable reaction vessel is added 116.0 grams of malic acid, 2.0 grams of tin oxide catalyst. 1171.0 grams of guerbet alkoxylate ester example #19. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 54

To a suitable reaction vessel is added 116.0 grams of malic acid, 2.0 grams of tin oxide catalyst. 1906.0 grams of guerbet alkoxylate ester example #20. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 55

To a suitable reaction vessel is added 160.0 grams of azelaic acid, 2.0 grams of tin oxide catalyst, 520.0 grams of guerbet alkoxylate ester example #21. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 56

To a suitable reaction vessel is added 160.0 grams of azelaic acid, 2.0 grams of tin oxide catalyst, 667.0 grams of guerbet alkoxylate ester example #22. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 57

To a suitable reaction vessel is added 160.0 grams of azelaic acid, 2.0 grams of tin oxide catalyst, 859.0 grams of guerbet alkoxylate ester example #23. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 58

To a suitable reaction vessel is added 132.0 grams of malonic acid, 2.0 grams of tin oxide catalyst, 1255.0 grams of guerbet alkoxylate ester example #24. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 59

To a suitable reaction vessel is added 132.0 grams of malonic acid, 2.0 grams of tin oxide catalyst, 1990.0 grams of guerbet alkoxylate ester example #25. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 60

To a suitable reaction vessel is added 132.0 grams of malonic acid, 2.0 grams of tin oxide catalyst, 660.0 grams of guerbet alkoxylate ester example #26. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 61

To a suitable reaction vessel is added 230.0 grams of dodecanedioic acid, 2.0 grams of tin oxide catalyst, 837.0 grams of guerbet alkoxylate ester example #27. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 62

To a suitable reaction vessel is added 230.0 grams of dodecanedioic acid, 2.0 grams of tin oxide catalyst, 999.0 grams of guerbet alkoxylate ester example #28. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 63

To a suitable reaction vessel is added 230.0 grams of dodecanedioic acid, 2.0 grams of tin oxide catalyst, 1395.0 grams of guerbet alkoxylate ester example #29. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 64

To a suitable reaction vessel is added 230.0 grams of dodecanedioic acid, 2.0 grams of tin oxide catalyst, 2130.0 grams of guerbet alkoxylate ester example #30. The temperature is then increased to 160–200 C. and by-product water begins to distill off. Vacuum is applied to keep the water distilling off. When 97% of the theoretical water is removed the reaction is cooled. The desired product is obtained without and additional purification.

EXAMPLE 65

A suggested utilization of the guerbet citrate ester of Examples 35–64 is conducted by using 0.12% by weight of the guerbet citrate ester, and following the general procedure given at Column 6 of U.S. Pat. No. 4,065,436.

By so following the general teachings of the aforementioned reference it will observed that the various guerbet citrate esters of the guerbet alcohols and their alkoxylates of the present invention give polycarbonates of high clarity and low volatility.

What is claimed is:

1. A polycarbonate resin composition containing an effective mold releasing amount of a guerbet citrate ester mold release agent conforming to the following structure:

$$\begin{array}{cc} R^1-O(O)CCH_2 & CH_2C(O)O-R^1 \\ | & | \\ R^2-O(O)CC-O-R-O-C-C(O)O-R^2 \\ | & | \\ R^3-O(O)CCH_2 & CH_2C(O)OR^3 \end{array}$$

R is selected from;

$$-\overset{O}{\overset{\|}{C}}-(CH_2)_n-\overset{O}{\overset{\|}{C}}-;$$

or $$-\overset{O}{\overset{\|}{C}}-(CH_2)_m-CH=CH(CH_2)_o-\overset{O}{\overset{\|}{C}}-;$$

n has a value from 1 to 15;
m and o independently range from 0 to 5;
$R^1$, $R^2$ and $R^3$ are independently selected from $$R^4-\overset{R^5}{\overset{|}{C}}HCH_2O-(EO)_x-(PO)_y-(EO)_z-;$$

wherein $R^4$ and $R^5$ may be the same or different saturated aliphatic groups; EO is ethylene oxide; PO is a propylene oxide group; x, y and z are independently between 0 and 10, said ethylene oxide being present in block or random manner by optionally premixing the oxides and the total carbon content of the alcohol derived portion of the molecule, in each instance, ranging from about 12 to about 40 carbon atoms.

2. The composition of claim 1 wherein $R^4$ and $R^5$ each independently range from $C_6H_{13}$ to $C_{10}H_{21}$ and x, y and z each independently range from 0 to 2.

3. The composition of claim 1 wherein
$R^4$ is $C_6H_{13}$,
$R^5$ is $C_{10}H_{21}$, and
x, y and z are each 0.

4. The composition of claim 1 containing from about 0.025% to about 1.0% by weight of the guerbet citrate ester.

5. A compound conforming to the following structure:

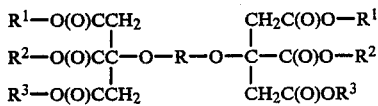

R is selected from;

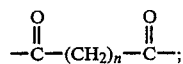

or

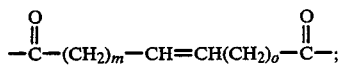

n has a value of 1 to 15;
m and o independently range from 0 to 5;
$R^1$, $R^2$ and $R^3$ independently selected from

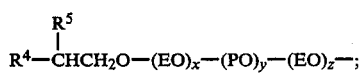

wherein $R^4$ and $R^5$ may be the same or different saturated aliphatic groups; EO is ethylene oxide; PO is a propylene oxide group; x, y and z are independently between 0 and 10, said ethylene and propylene oxide being present in block or random manner by optionally premixing the oxides and the total content of the alcohol derived portion of the molecule, in each instance, ranging from about 12 to about 40 carbon atoms.

6. The compound of claim 5 wherein $R^4$ and $R^5$ each independently range from $C_6H_{13}$ to $C_{10}H_{21}$ and x, y and z each independently range from 0 to 2.

7. The compound of claim 5 wherein
$R^4$ is $C_6H_{13}$,
$R^5$ is $C_{10}H_{21}$, and
x, y and z are each 0.

8. A compound conforming to the following structure:

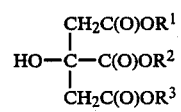

wherein;
$R^1$, $R^2$ and $R^3$ are independently selected from;

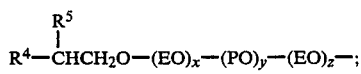

$R^4$ and $R^5$ may be the same or different saturated aliphatic groups;
EO is ethylene oxide, PO is a propylene oxide group, x, y and z are independently between 0 and 10 and the total carbon content of the alcohol derived portion of the molecule, in each instance, ranging from about 12 to about 40 carbon atoms.

9. The compound of claim 8 wherein $R^4$ and $R^5$ each independently range from $C_6H_{13}$ to $C_{10}H_{21}$ and x, y and z each independently range from 0 to 2.

10. The compound of claim 8 wherein
$R^4$ is $C_6H_{13}$,
$R^5$ is $C_{10}H_{21}$, and
x, y and z are each 0.

* * * * *